United States Patent [19]

Donnelly et al.

[11] 4,394,237
[45] Jul. 19, 1983

[54] SPECTROSCOPIC MONITORING OF GAS-SOLID PROCESSES

[75] Inventors: Vincent M. Donnelly, Berkeley Heights; Daniel L. Flamm, Chatham Township, Morris County; Robert F. Karlicek, Jr., Kenilworth, all of N.J.

[73] Assignee: Bell Telephone Laboratories, Incorporated, Murray Hill, N.J.

[21] Appl. No.: 284,468

[22] Filed: Jul. 17, 1981

[51] Int. Cl.³ .............................................. C23C 15/00
[52] U.S. Cl. ............................ 204/192 E; 204/192 R; 204/298; 156/345; 156/643
[58] Field of Search ...................... 204/192 E, 192 R; 156/643, 345

[56] References Cited

U.S. PATENT DOCUMENTS

| | | | |
|---|---|---|---|
| 3,654,109 | 4/1972 | Hohl et al. | 204/298 |
| 3,734,620 | 5/1973 | Cade | 204/298 |
| 4,140,078 | 2/1979 | Wilmanns | 204/298 |
| 4,166,784 | 9/1979 | Chapin et al. | 204/192 R |
| 4,172,020 | 10/1979 | Tisone et al. | 204/192 R |
| 4,198,261 | 4/1980 | Busta et al. | 204/192 E |
| 4,208,240 | 6/1980 | Latos | 204/298 |
| 4,246,060 | 1/1981 | Keller | 156/345 |
| 4,263,088 | 4/1981 | Gorin | 204/192 E |
| 4,281,030 | 7/1981 | Silfvast | 204/192 R |
| 4,312,732 | 1/1982 | Degenkolb et al. | 156/643 |

OTHER PUBLICATIONS

Donnelly et al., J. Chem. Phys., 66, (1977), pp. 4100–4109.
Ratinen, J. Appl. Phys., 44, (1973), pp. 2730–2733.
White et al., Science, 177, (1972), pp. 481–486.
Greene et al., J. Vac. Sci. Technol., 10, (1973), pp. 1144–1148.

*Primary Examiner*—Arthur P. Demers
*Attorney, Agent, or Firm*—Bruce S. Schneider

[57] ABSTRACT

A method for accurately monitoring and adjusting gas phase processes such as gas etching and chemical vapor deposition has been found. This method relies on the use of induced fluorescence. The gaseous phase used in the process to be monitored is probed by excitation with a suitable energy source. The emission from the gas phase induced through this excitation is then monitored and yields an accurate measure of concentration of the active species present. In turn the conditions of the fabrication process are adjusted based on these discerned concentrations.

14 Claims, 2 Drawing Figures

SPECTROSCOPIC MONITORING OF GAS-SOLID PROCESSES

BACKGROUND OF THE INVENTION

1. Field of the Invention

This invention relates to processes involving gas-solid interaction, and, in particular, such processes utilized in fabricating devices.

2. Description of the Prior Art

A variety of techniques involving gas-solid interactions are employed in fabrication of devices such as semiconductor devices. For example, in preparation for a subsequent metallization, a semiconductor material often is etched to produce grooves in a desired pattern on its surface. One desirable etching procedure, discharge etching, involves subjecting a material to an electrical discharge or to species obtained through an electrical discharge. (In this context an electrical discharge is an ionized or partially ionized gas sustained by an electrical field such as that produced by the application of a D.C. potential, a radio frequency electrical field, or electromagnetic radiation.) Another etching process involves the production of etching species in a gas or at a gas-solid interface by treatment with a high intensity optical source such as a laser. In these processes an etchant resistant delineating material is generally deposited onto a device precursor, i.e., a structure being processed into a device. The delineating material is then patterned by conventional techniques such as photolithography so that a desired pattern is defined by the remaining portions of the delineating material. When the device precursor with its delineating layer is treated with the etchant, those portions of the device precursor that are not covered by the delineating material are removed. By choosing an appropriate etchant gas, for example, a gas in an electrical discharge at relatively low partial pressure levels, i.e., below 20 Torr, it is possible to keep the walls of the etched region substantially vertical. Thus, the pattern of the delineating material is faithfully reproduced in the device precursor by utilizing a process depending on gas-solid interaction.

The device precursor being treated by procedures such as discharge etching is often formed through other processes that involve gas-solid interactions. For example, chemical vapor deposition (CVD) is a common technique utilized for producing relatively uniform layers of semiconductor material, e.g., III-V or II-VI semiconductor materials. In the case of a CVD procedure, the deposition of a solid is induced on a substrate by producing gradients such as thermal or concentration gradients between the gas and the surface of the substrate. If the gas has appropriate constituents, the desired material is deposited on the substrate. For example, for the deposition of GaAs, HCl is passed over liquid Ga to produce a gas including GaCl. A mixture of this gas containing GaCl with gaseous $AsH_3$ is flowed through a heated region that includes solid material upon which deposition is desired. Contact with the heated material induces the formation of GaAs on the surface.

Fabrication processes such as CVD and electrical discharge etching, e.g., reactive ion etching, reactive sputter etching and plasma etching, that rely on gas-solid interactions are crucial to the production of a variety of commercially significant devices. It is quite important to control these fabrication processes so that devices are produced that each have essentially uniform electrical and physical properties. In the context of a CVD process, the quality and reproducibility of a deposited semiconductor layer strongly depend on the careful control of the process parameters. Similarly, the quality of the pattern (e.g., the faithful reproduction of a desired pattern) produced by a gas etching technique also strongly depends on the careful control of process parameters.

Numerous methods have been postulated for monitoring an individual gas phase component present in a fabrication process relying on gas-solid interactions. The ultimate goal is to adjust the fabrication process conditions with the information obtained through this monitoring to yield a desirable gas composition, i.e., a suitable concentration for each gaseous component, and to yield a desired and reproducible end result. Often monitoring procedures rely on absorption or emissive spectroscopic techniques since such procedures do not generally perturb the composition of the gas phase being monitored. (In contrast, mass spectroscopic techniques have been employed in monitoring CVD and discharge etching processes. See Ban, *Journal of the Electrochemical Society*, 118 (9), 1473 (1971). If the sample inlet for the mass analyzer is near the material being processed, generally, it will significantly perturb the gas and thus substantially influence the procedure. See T. O. Sedgwick, *Journal of Crystal Growth*, 31, 264 (1975). If, however, to avoid this problem the analyzer is removed from this area, the composition of the gas when it reaches the analyzer often differs significantly from the composition of the gas being sampled.)

In the context of etching processes, light emissions from the gas, in the infrared, visible and ultraviolet region of the spectrum, have been monitored to detect the completion of the etching process by measuring the qualitative presence or the absence of a particular component. (See, for example, U.S. Pat. No. 3,664,942 issued May 23, 1972.) In one such procedure the etching of a layer produces gas phase components that are derived from materials present in the layer being etched, e.g., if InP is being etched by a chlorine containing plasma, gaseous indium chloride is produced. When the etching has progressed through the entire thickness of the layer being etched, e.g., an InP layer, a component corresponding to a material in the etched layer but not in the underlying layer, e.g., indium chloride, will no longer appear in the gas phase. Thus an indication of the complete etching through this layer is provided.

In an alternative method, the substantial absence or qualitative presence of an etchant species is monitored. For example, if a silicon layer is etched in a fluorine discharge, atomic fluorine will be essentially absent as long as there is Si available for reaction with the fluorine. When the silicon layer is etched through, the fluorine concentration becomes significantly larger since it is not being consumed by reaction with silicon. Although such qualitative techniques are desirable for end-point detection, they yield little information that is useful in controlling the quality of the process, e.g., the accuracy of the pattern replication. Generally, as previously discussed, the quality of a device produced by a given procedure depends on the relative concentration of a particular species and not merely on its presence or absence.

Monitoring schemes requiring a more sensitive measure of gas component concentration have been considered. Attempts have been made to measure the quantitative concentration of species present in the gas phase during CVD fabrication. Specifically, Raman scattering spectroscopy has been employed. (See J. E. Smith, Jr. and T. O. Sedgwick, *Thin Solid Films*, 40, 1 (1977). However, adequate control of a CVD process generally necessitates the simultaneous monitoring of a plurality of gas phase components, i.e., monitoring of two or mores species in a time period less than the deposition time, preferably less than a tenth of the deposition time, most preferably less than one-hundredth of the deposition time. This requirement is especially important in the monitoring of the CVD processes for compound semiconductor materials such as III-V or II-VI semiconductor materials or the ternaries or the quaternaries of these semiconductor materials. Raman spectroscopy, in theory, should allow such simultaneous monitoring. Despite this prediction, Sedgwick reported that Raman spectroscopy is ineffective because fluorescence induced by the laser excitation source of the Raman spectrometer completely masked the Raman signal. Since the induced fluorescence was so intense, it was natural to consider laser emission spectroscopy, i.e., the detection of fluorescence following the absorption of light from a laser excitation source. Attempts to employ laser induced fluorescence were also abandoned when simultaneous monitoring of a plurality of gas components was not achieved.

In etching processes, as opposed to CVD processes, the monitoring of a plurality of components is not always essential. However, in the presence of a discharge or a plurality of emitting species, monitoring the concentration of even one component poses many difficulties. The highly energetic gas itself produces an extremely high level of electromagnetic emissions. These emissions typically are not suitable as a quantitative monitoring expedient. Often the emitting species are not the ones whose concentration gives a measure of process quality. Additionally, the intensity of emissions such as discharge emissions depends not only on the concentration of emissive components but also on the availability of energetic electrons to excite these components. The extent of electron/component interactions is not controllable and varies with many process conditions. (See J. W. Coburn, M. Chen, *Journal of Vacuum Science and Technology*, 18, 353 (1981) and C. J. Mogab et al., *Journal of Applied Physics*, 49, 3796 (1978).) Since electron/component interactions vary irregularly with changes in many important process conditions, such as gas pressure or component concentration and since the dependence of electron/component interactions on process conditions is typically unknown, the emission intensity generally yields no easily discernible information concerning control of etching processes. The high energy excitation of the gas in etching processes and the possible large spatial gradients associated with high energy processes also appear to suggest difficulty in the adequate spectroscopic monitoring of etching processes. Thus, in general, adequate quantitative monitoring of the concentrations of components in processes involving gas-solid interactions is not a reality.

SUMMARY OF THE INVENTION

Induced emission spectroscopy offers a nonintrusive method of quantitatively measuring the concentration of gas phase components. The procedure avoids the problems associated with the energetics of gas etching processes when a pulsed excitation irradiation is used. Additionally, induced fluorescence allows the simultaneous monitoring of a plurality of gas components in either a gas etching method or significantly in a CVD process, provided exciting energy is utilized that is sufficiently energetic and sufficiently intense to induce at least one fragmentation process (ionization or dissociation) and/or to induce at least one multiple photon processes. For example, the simultaneous concentration of species such as $PH_3$, $P_2$, $AsH_3$, $As_2$, $As_4$, $InCl$ and $GaCl$ at relatively low concentrations, i.e., lower than $10^{-4}$ atm in 1 atm of a $H_2$ carrier gas, is measurable.

DETAILED DESCRIPTION

Figure 1:
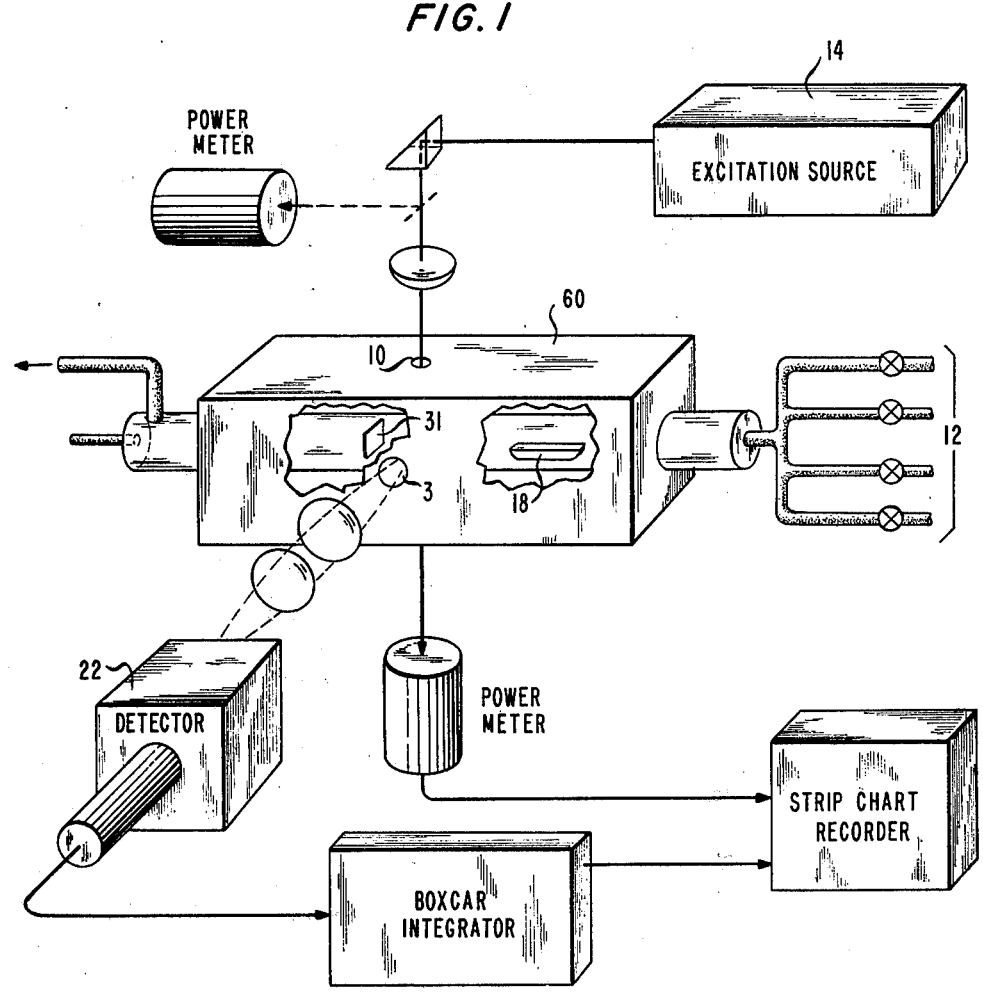
FIGS. 1 and 2 illustrate apparatuses suitable for the practice of the invention.

The use of an induced fluorescence technique results not only in a nonintrusive quantitative method of monitoring gas phase reactions, but also with a suitable choice of excitation energies allows simultaneous monitoring of a plurality of components. Thus adequate control of gas-solid interaction processes involving CVD is possible. The use of an induced fluorescence technique with a pulsed excitation irradiation also allows control of energetic gas etching processes. Further the laser induced technique is useful for monitoring a localized region of a gas employed in a device fabrication process. For example, in a discharge etching process, it is possible to produce a plasma in a gas phase etchant by conventional techniques such as by a radio frequency discharge. Such a plasma typically has dimensions of at least 3 to 50 cm. The chemical components in the plasma neighboring (within 0.5 cm) of the substrate, 44 in FIG. 2, being etched often determines the efficacy of the etching process. Significantly, using induced fluorescence it is possible to monitor the chemical components in this localized area rather than detecting an average of concentration of the components throughout the discharge. Similarly, a measurement of the concentration of chemical components, in a CVD process, that are in the vicinity of the substrate, 31 in FIG. 1, upon which deposition is occurring, generally yields a better indication of process quality.

Generally, the concentration of a species is proportional to the observed fluorescence intensity, provided corrections for quenching (when necessary) and for laser intensity variations are made. The latter correction is made by using the power dependence relationship of the concentration of the fluorescing species upon the excitation source intensity at the point of observation. (The power law dependence is obtained as described by McDonald et al., *Chemical Physics* 33, 161 (1978) and the intensity at the point of observation is calculated through Beers law as described by J. G. Calvert and J. N. Pitts, *Photochemistry*, Wiley & Sons, pp. 21, 22 (1966).) The intensity of the excitation source output and the intensity of the beam after it passes through the apparatus are measured. The correction for this measured variation of intensity at the point of observation is continuously applied during monitoring using the power dependence relationship previously obtained.

Similarly correction for quenching is also made. The concentration of each species that quenches the fluorescence to be monitored is determined under the process conditions being employed. (This determination is done by measuring fluorescence intensity of each of these quenching species and making the excitation source intensity correction described above.) Using the relationship described by V. M. Donnelly, et al. *Journal of Chemical Physics,* 71, 659 (1979) and using the quenching rate constants for this relationship as measured by the techniques described in V. M. Donnelly and F. Kaufman, *J. Chem. Phys.,* 66 4100 (1977), this correction is completed. (Where inert components dominate as the quenching species and the pressure of these inert species is constant, the quenching correction is a constant.)

If absolute concentrations are desired, a calibration for instrument response factors such as detector efficiency and a correction for quantum yield, i.e., the ratio of the number of absorbed photons to the number of emitted photons at the fluorescence wavelength of the species being measured are necessary. Instrument factors are determined by using a controlled sample. A gas having well-known spectroscopic properties such as $NO_2$ or $NH_3$ is introduced into the system. (See J. R. McDonald et al., *Chemical Physics,* 43, 271 (1979). For this sample gas a measurement of the fluorescence intensity per unit intensity of the excitation source at the point of measurement yields the instrument calibration factor. Quantum yield is measured as described by J. G. Calvert and J. N. Pitts supra pp. 798-804.)

As discussed induced fluorescence is particularly suited to monitoring species concentration in a specific area of a gas. The fluorescence observed is from species excited in the volume of gas illustrated by the excitation source. Therefore, this fluorescence is indicative of the concentration of species in the illuminated region. Beam diameters for lasers of less then 10 $\mu$m are easily achievable. Therefore, absorption regions as small as 10 $\mu$m in cross-section are practical. In many cases, substantially all induced emissions occur in the region of absorption. In this situation the use of a focused detection system allows resolution of volumes down to 1 $mm^3$ or less, essentially anywhere within the boundaries of the gas being sampled. (Generally, it is advantageous to monitor the region in proximity to the substrate. However, in some monitoring processes, such as described in Ban supra, it is desirable to monitor species downstream from the substrate in either a CVD or gas etching process. This is also possible by using induced fluorescence and is not precluded.)

To induce fluorescence, the exciting energy, e.g., laser light, should be incident on the volume of gas to be monitored. This requirement is expeditiously satisfied by installing a window, 10 in FIGS. 1 and 2, of suitable material on the walls of the apparatus being used in the fabrication process. For presently available source intensities the material used for this window should generally have a transmission larger than 5 percent, for the spectral region of the exciting energy. For example, quartz should be employed for radiation in the range 170 nm to 4500 nm and in addition to these materials $CaF_2$ is suitable for radiation in the range of 130 nm to 9000 nm. Exemplary apparatus configurations useful in CVD and gas phase etching process are shown respectively in FIGS. 1 and 2.

The source of excitation energy should be chosen to be in an appropriate spectral region and to have sufficient intensity in this region to induce a level of fluorescence that is detectable Generally, fluorescence intensities greater than 10 photon counts per second are detectable. This level of detection typically is achievable by using an excitation intensity in the desired spectral region above approximately 10$\mu$ Joules per sec in the measurement region. The energy of the excitation source should also be carefully chosen. In order to simultaneously monitor a plurality of chemical components, specific processes that lead to light emission should be induced in the gases associated with the chemical vapor deposition process. The exciting light should be of sufficiently short wavelength to induce at least one fragmentation and/or at least one multiple photon process in the gas components. (Fragmentation processes as used in this context, include ionization—the gas is fragmented into an ion and an electron—and also includes dissociation processes—a component is fragmented into two entities which include atoms, ions, or molecules. Multiple photon processes in this context include processes which lead to fluorescence through the absorption of at least two photons of light.) Exemplary of ionization procsses, dissociation processes, and multiple photon processes which give rise to discrete emission frequencies in the context of III-V CVD deposition are:

Ionization

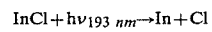

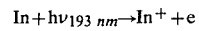

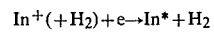

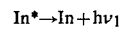

Dissocation

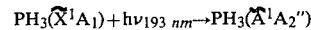

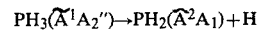

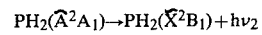

Multiple Photon

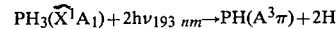

or

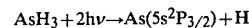

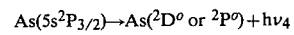

In the simultaneous monitoring technique of the inventive process, at least one of the components and preferably several components are monitored through these fragmentation or multiple photon mechanisms. To satisfy this requirement generally, electromagnetic radiation with a photon energy in the spectral region between 3 eV and 12 eV is used. Light with sufficient energy for dissociation, ionization, or multiple photon processes is employed. The former two processes result in fragmentation. There are so many absorbing states generally above the dissociation or ionization energy of a species that essentially any photon with energy above these limits is absorbed. Thus, in general, light with energy in excess of that need for dissociation or ionization is useful. Multiple photon processes because of their typically lower cross sections are usually not considered useful for monitoring techniques. However, has been found in the framework of CVD and gas etching processes that multiple photon processes result in detectable emissions. These processes further expand the choice of a suitable excitation source. Additionally, since a multiple photon process often induces ionization and dissociation, the range of wavelengths, as explained above, for exciting these processes is even broader. A further advantage of inducing a fragmentation and/or a multiple photon process is flexibility in the choice of a single rather than a plurality of exciting sources to produce the simultaneous absorption, emission, and thus monitoring of a plurality of species. (Although use of a single source is advantageous, the use of a plurality of sources is not precluded.)

The energy necessary for excitation is easily ascertained for species generally employed in CVD processes. The ionization potential of the various components to be monitored, the dissociation energies and the photon energy employable for multiple photon processes are available from many tabulations such as K. P. Huber and G. Herzberg, *Molecular Spectra and Molecular Structure*, "IV Constants of Diatomic Molecules", Van Nostrand Reinhold Company, New York 1979; R. W. B. Pearse and A. G. Gaydon, *Identification of Molecular Spectra*, 4th Ed., Chapman and Hall Ltd., London, 1976; and the *Handbook of Chemistry and Physics*, Chemical Rubber Co., Cleveland Ohio, 1967. For monitoring gas etching processes the region between 1 eV and 12 eV is generally useful. The specific spectral region employed in a gas etching process depends on the particular composition of the gas being used. Spectroscopic constants indicating suitable wavelengths for the excitation of a wide variety of chemical entities used in gas etching have been compiled. (See, for example, Huber and Herzberg supra, and Pearse and Gaydon supra.) The possible fluorescence frequencies for species such as those present in either CVD or gas etching processes have also been reported in innumerable sources. (See, for example, Huber and Herzberg supra and Pearse and Gaydon supra.) The spectral region is chosen so that absorption in the desired entity to be monitored is produced and so that this absorption yields a measurable fluorescence level.

Exemplary of suitable excitation sources are excimer lasers such as the ArF excimer laser which produces 193 nm emission for the monitoring the CVD processes involving III-V compounds, e.g., InP, GaAs, ternaries such as $Ga_xIn_{1-x}As_y$ and quaternaries such as $Ga_{x-}In_{1-x}As_yP_{1-y}$. Exemplary of excitation sources suitable for the monitoring of plasma processes such as $Cl_2$ etching processes is a tunable dye laser. The larger intensities available with laser excitation sources lead to totally adequate levels of induced emission. However, for species that have large absorption cross-sections and correspondingly intense allowed emission transitions the use of diffuse excitation source such as a resonance lamp or arc source is not precluded.

Exemplary of chemical vapor deposition processes are those involving the deposition of InP. In such processes, the gas that is introduced at 12 in FIG. 1 flows over the substrate and typically includes InCl, $PH_3$, $P_2$ and $P_4$. (The InCl is typically produced by passing HCl over boat, 18, containing In.) By the use of an excitation source, 14, such as the 193 nm ArF laser, the following spectroscopic processes occur:

$$PH_3(\tilde{X}^1A_1) + h\nu_{193\ nm} \rightarrow PH_3(\tilde{A}^1A_2'') \rightarrow PH_2(\tilde{A}^2A) + H$$

$$PH_2(\tilde{A}^2A_1) \rightarrow PH_2(\tilde{X}^2B_1) + h\nu;$$

$$PH_3(\tilde{X}^1A_1) + 2h\nu_{193\ nm} \rightarrow PH(A^3\pi) + 2H$$

$$PH(A^3\pi) \rightarrow PH(X^3\Sigma^-) + h\nu,$$

$$P_2(X^1\Sigma_g^+, v''=0) + h\nu_{193\ nm} \rightarrow P_2(C^1\Sigma_u^+, v'=11)$$

$$P_2(C^1\Sigma_u^+, v'=11,10,9,8,7)P_2(X^1\Sigma_g^+, v''=0-33) + h\nu,$$

and the series $$InCl + h\nu_{193} \rightarrow In + Cl$$

$$In + h\nu_{193} \rightarrow In^+ + e$$

$$In^+ (+H_2) + e \rightarrow In^* (+H_2)$$

$$In^* \rightarrow In + h\nu.$$

By using a single source, e.g., 193 nm excimer laser and simultaneously monitoring the indicated emissions with detector, 22, the simultaneous measurement of concentrations of the important species in InP deposition is effected.

In a gaseous etching process, there are also generally numerous emissions that are available for monitoring. Emissions from a discharge or from highly energetically excited gases interfere with detection of induced fluorescence. However, by using a pulsed excitation source, 40 in FIG. 2, and by detecting emission only immediately after the excitation pulse, the interference from the discharge emissions are effectively eliminated. Generally, excitation pulses having a duration less than 1 msec are employed. For pulse durations less than 1 msec, detection within 1 msec of the termination of the pulse is desirable. (Termination of the pulse occurs when the desired excitation energy falls to below one-third of its peak value.) Using this expedient, emissions such as those from InCl induced in a chlorine containing etching plasma in region 41 near substrate 44 placed on a grounded electrode, 42, for an In containing material are detectable. Using the induced emission technique there is ample observable emission intensity.

The monitoring of emissions in either CVD or gas etching processes is done expeditiously through a second window, 3, in the fabrication apparatus that is disposed at an angle, e.g., approximately 90 degrees from the window, 10, used for excitation. In this manner the amount of scattered light from the excitation source that is detected is substantially reduced. The means of detection, 22, is not critical. Typically, a photomultiplier tube or photodiode used either with a monochromator or a filter system is employed. Where a plurality of emissions are detected simultaneously, an optical multichannel analyzer, several monochromatic detectors, or an array of photodiodes with a monochromator are advantageously used as a detection system.

As discussed, the monitoring of species in the gas phase is useful for controlling fabrication processes involving gas-solid interactions. For example, in the case of gas etching of In-containing, e.g., InP or Ga-containing, e.g., GaAs semiconductor materials utilizing a Cl-containing plasma produced by an energy source, 55, such as a r.f. generator, excitation with light of 349 nm and 403 nm wavelength, respectively, and detection of InCl and Ga emission, respectively, at approximately 363 nm and 417 nm, respectively, allows control of the etching process. (It is also possible to monitor emissions for As and P species.) Also, the properties of materials such as III-V semiconductors deposited by chemical vapor deposition are reproducible by ensuring that the concentration of the various components, e.g., $PH_3$, $P_2$, $AsH_3$, $As_2$, InCl and GaCl in the growth of $Ga_xIn_{1-x}As_yP_{1-y}$ are present in concentrations that yield the desired properties in the deposited semiconductor layer. Thus, the invention involves controlling the fabrication of a device through the monitoring of concentrations of gas phase components utilized in the fabrication of these devices.

The following examples demonstrate suitable wavelengths for excitation and detection of significant species.

EXAMPLE 1

Figure 2:
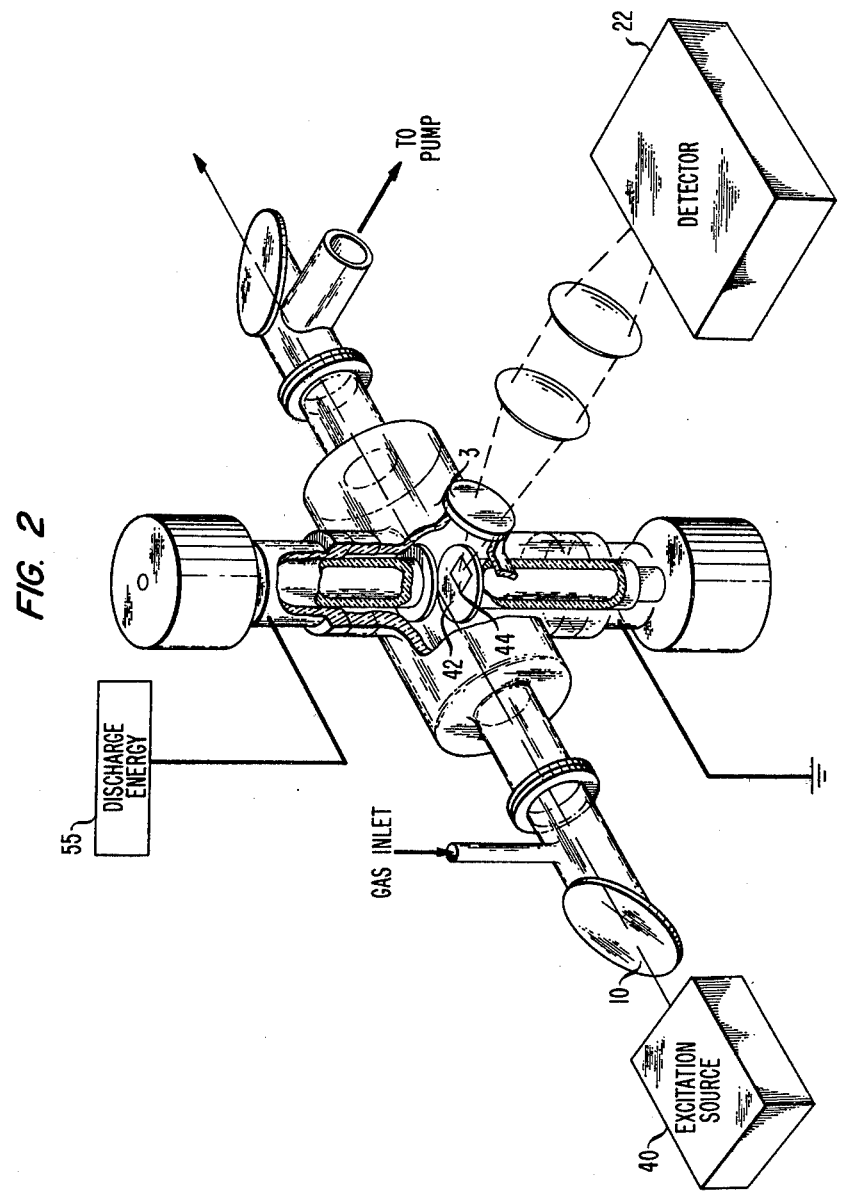

The apparatus shown in FIG. 1 was employed. The boat, 18, was filled with In having a purity of 99.999 percent and placed in the apparatus as shown in FIG. 1. The deposition chamber was evacuated with a roughing pump and the furnace, 60, was employed to heat the chamber to 700 degrees C. Hydrogen of purity 99.999 percent was introduced through the tubes at 12 and flowed through the chamber at a rate of 500 standard cubic centimeters per minute (sccm). The beam from an ArF excimer laser was directed through window, 10, into the deposition area near the substrate holder. A three-tenths meter grating monochromator, 22, was set to pass radiation having a wavelength of 451 nm. (At this point a measurable signal was obtained indicating the level of In vapor from the boat, 18.) Sufficient HCl was introduced through the tubes at 12 that its percentage of the total gas flow was 0.1 percent. (The total gas pressure was 1 atmosphere.) The level of fluorescence was noted.

The HCl flow was terminated and the system was purged by the continuing hydrogen flow. The HCl flow at the same level was reinitiated and a strip chart recording of the variation of fluorescence intensity with time from the reinitiation of the HCl flow was made. The time to establish steady-state concentration of InCl was 55 seconds. (It should be noted that a side benefit of this measurement is the realization that process conditions should be adjusted so that InP deposition on the substrate is not initiated until at least 55 seconds after the introduction of HCl into the system.

EXAMPLE 2

The procedure of Example 1 was followed except a metal was not placed in the boat, 18. The gas flow employed was a mixture of arsine and hydrogen in a proportion of approximately 1 to 1000 with a total pressure of 1 atmosphere and a total flow of 1000 sccm. The temperature utilized was 813 degrees C, the excitation source was a KrF excimer laser (248 nm), the detector was set at 289 nm, and fluorescence from $As_2$ was detected. The arsine flow was terminated while the hydrogen flow was continued. The change of fluorescence with time from the termination of the arsine flow was monitored. Approximately 4 minutes was required for a 4-fold decrease in the intensity of the monitored fluorescence. (Thus, as an additional benefit it was determined that at the termination of growth in a CVD process involving arsenic compounds, the continued presence of arsenic is possible from deposits on the deposition chamber. Therefore, precautions are necessary to clean the chamber to prevent this occurrence.)

EXAMPLE 3

The procedure of Example 2 was followed except the arsine concentration was 0.2 percent. Two detectors were employed, one at 235 nm to monitor As emission and one at 623 nm to monitor $AsH_2$ emission.

What is claimed is:

1. A process for fabricating devices comprising the steps of introducing a gas into proximity to a material surface, inducing a change in said material surface, spectroscopically monitoring said gas and controlling said process in accordance with said spectroscopic monitoring characterized in that the quantitative concentration of a plurality of species in said gas is monitored by inducing fluorescence from said plurality of species with a light source external to said gas wherein at least one of said species fluoresces through a spectroscopic fragmentation process or multiple photon process, and wherein based on the quantitative measurement of said fluorescence the conditions of said fabrication process are adjusted to yield a desired result.

2. The process of claim 1 wherein said process comprises a chemical vapor deposition process.

3. The process of claim 2 wherein a material chosen from the group of semiconductor materials consisting of III-V compounds, II-V compounds and quaternaries and ternaries thereof is deposited.

4. The process of claim 1 wherein said fabrication process comprises a gas etching process.

5. The process of claim 4 wherein said process comprises an electrical gas discharge etching process.

6. The process of claim 5 wherein said process comprises a reactive ion etching process.

7. The process of claim 1 wherein said fluorescence is induced using a laser.

8. The process of claim 1 wherein said laser is an excimer laser.

9. The process of claim 7 wherein said laser comprises an ArF laser.

10. The process of claim 9 wherein said fluorescence results from a material chosen from the group consisting of indium-containing, gallium-containing, arsenic-containing and phosphorous-containing species.

11. A process for fabricating devices comprising the steps of introducing a gas into proximity to a material surface, inducing a change in said material surface, spectroscopically monitoring said gas and controlling said process in accordance with said spectroscopic monitoring characterized in that species that etch the composition of said surface of said material are produced, fluorescence of at least one of said etching species is induced by using an external pulsed light excitation source, a quantitative measure of said etching species is made by monitoring said fluorescence at a time when said source excitation has terminated, and based on said quantitative measure said fabrication process is adjusted to yield a desired result.

12. The process of claim 11 wherein said gas is a chlorine containing gas.

13. The process of claim 11 wherein said surface contains a member of the group consisting of indium phosphorous, arsenic and gallium species.

14. The process of claim 11 wherein said etching species is produced by electrical discharge.

* * * * *

UNITED STATES PATENT AND TRADEMARK OFFICE
CERTIFICATE OF CORRECTION

PATENT NO. : 4,394,237
DATED : July 19, 1983
INVENTOR(S) : Vincent M. Donnelly, Daniel L. Flamm, and Robert F. Karlicek, Jr.

It is certified that error appears in the above—identified patent and that said Letters Patent is hereby corrected as shown below:

Column 6, line 16, "procsses" should read --processes--; line 63, "has" should read --it has--. Column 8, line 3, "$\Sigma_g^+$" should read --$\Sigma_g^+$--; "$\Sigma_u^+$" should read --$\Sigma_u^+$--; line 5, "$\Sigma_u^+$" should read --$\Sigma_u^+$--; "$\Sigma_g^+$" should read --$\Sigma_g^+$--.

Signed and Sealed this

First Day of November 1983

[SEAL]

Attest:

Attesting Officer

GERALD J. MOSSINGHOFF

Commissioner of Patents and Trademarks